United States Patent [19]

Schumann et al.

[11] Patent Number: 5,620,411

[45] Date of Patent: *Apr. 15, 1997

[54] ANKLE BRACE WALKER

[75] Inventors: Gail H. Schumann; Vernon L. Stevenson, both of Fort Worth, Tex.

[73] Assignee: Tecnol Medical Products, Inc., Fort Worth, Tex.

[*] Notice: The term of this patent shall not extend beyond the expiration date of Pat. No. 5,352,189.

[21] Appl. No.: 250,271

[22] Filed: May 27, 1994

Related U.S. Application Data

[63] Continuation of Ser. No. 838,608, Feb. 19, 1992, Pat. No. 5,352,189.

[51] Int. Cl.⁶ ............................................. A61F 5/00
[52] U.S. Cl. ........................ 602/23; 602/27; 128/882
[58] Field of Search ............................. 128/846, 882, 128/DIG. 20, DIG. 15, 869; 602/5, 23, 26, 27

[56] References Cited

U.S. PATENT DOCUMENTS

| | | | |
|---|---|---|---|
| Re. 33,395 | 10/1990 | Peters | 128/80 |
| 3,955,565 | 5/1976 | Johnson, Jr. | 128/89 |
| 4,280,489 | 7/1981 | Johnson, Jr. | 128/80 |
| 4,378,793 | 4/1983 | Maudlin et al. | 128/80 |
| 4,414,965 | 11/1983 | Maudlin et al. | 128/87 |
| 4,433,679 | 2/1984 | Maudlin et al. | 128/80 |
| 4,446,856 | 5/1984 | Jordan | 128/80 |
| 4,494,534 | 1/1985 | Hutson | 128/80 |
| 4,510,927 | 4/1985 | Peters | 128/80 |
| 4,517,968 | 5/1985 | Greene et al. | 128/80 |
| 4,572,169 | 5/1986 | Maudlin et al. | 128/80 |
| 4,587,962 | 5/1986 | Greene et al. | 128/80 |
| 4,771,468 | 9/1988 | Crispin | 128/88 |
| 4,834,078 | 5/1989 | Biedermann | 128/80 |
| 4,865,023 | 9/1989 | Craythorne et al. | 128/80 |
| 4,919,118 | 4/1990 | Morris | 128/88 |
| 4,934,355 | 6/1990 | Procelli | 602/27 |
| 4,938,777 | 7/1990 | Mason et al. | 623/50 |
| 4,962,760 | 10/1990 | Jones | 128/80 |
| 4,966,134 | 10/1990 | Brewer | 128/80 |
| 4,974,583 | 12/1990 | Freitas | 128/80 |
| 5,031,607 | 7/1991 | Peters | 128/80 |
| 5,050,620 | 9/1991 | Cooper | 602/27 |
| 5,056,509 | 10/1991 | Swearington | 128/80 |
| 5,078,128 | 1/1992 | Grim et al. | 128/83.5 |
| 5,088,480 | 2/1992 | Wang | 602/27 |
| 5,094,232 | 3/1992 | Harris | 602/27 |

*Primary Examiner*—Michael A. Brown
*Attorney, Agent, or Firm*—Baker & Botts, L.L.P.

[57] ABSTRACT

Load forces are distributed and reacted along lateral and medial side plates, thereby avoiding the concentration of stresses which could cause cracking, buckling, crippling and the like. This is provided by an intermediate plate portion which has an external edge in the form of an elliptical segment. Because of the elliptical profile of the intermediate side plate portion, shear forces imposed by an applied toe load will be distributed through the intermediate side plate portion, thereby reducing the maximum level of forces imposed at the union of lateral and medial brace members with lateral and medial side plates. The gait pattern of the patient is accommodated by a composite outsole which permits yieldable, bending contact rather than rigid, rolling contact with the ground surface. The composite outsole includes an elongated, flexible shell, a flexible heel core and a flexible foot core, with the flexible heel core and foot core being enclosed within the flexible shell in tandem relation to each other. A fulcrum line is established at the interface of the heel core and foot core. The composite, flexible outsole is bendable laterally and medially with respect to the longitudinal centerline, thereby accommodating lateral or medial toe walk gait aspects.

33 Claims, 5 Drawing Sheets

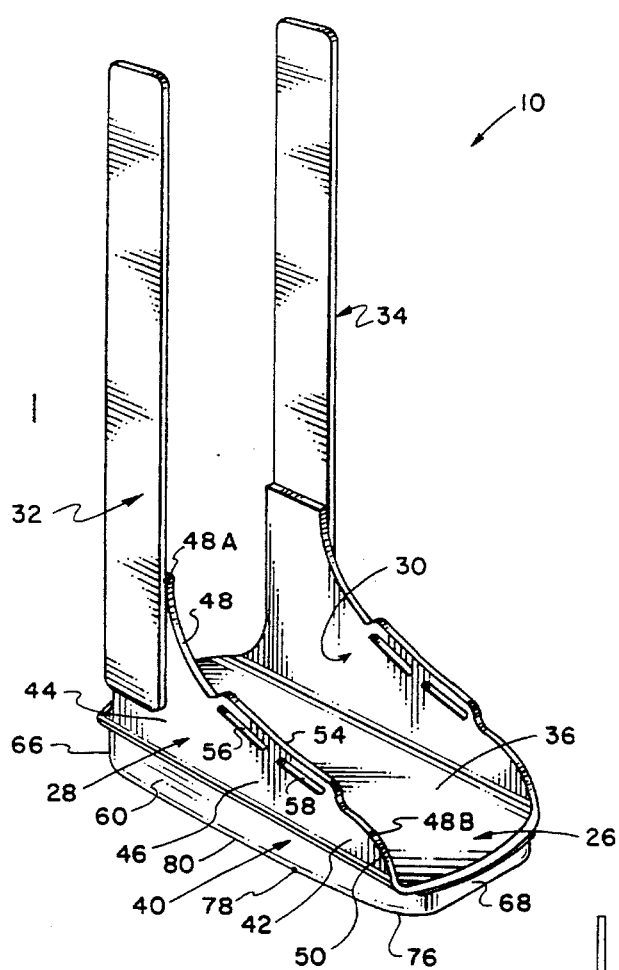
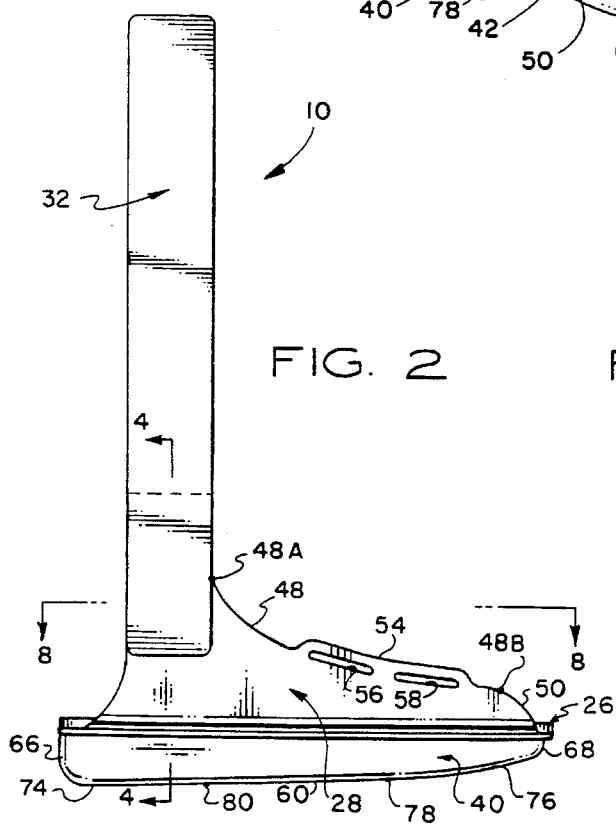
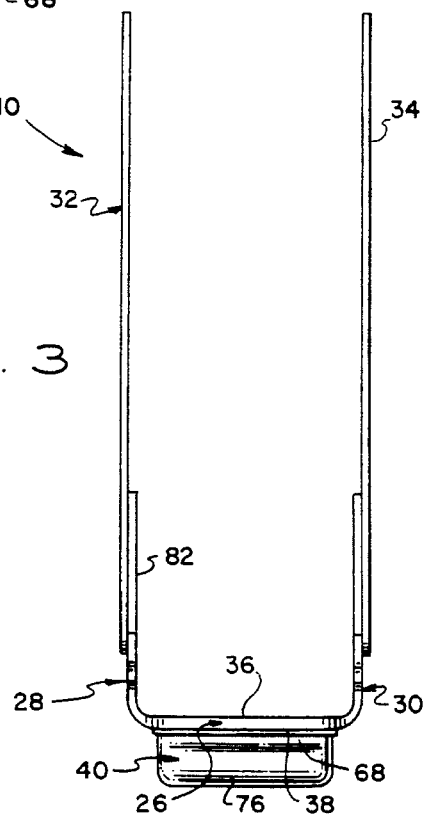

ANKLE BRACE WALKER

CROSS REFERENCE TO RELATED APPLICATIONS

This application is a continuation application of U.S. application Ser. No. 07/838,608, filed Feb. 19, 1992 and entitled "Ankle Brace Walker", now U.S. Pat. No. 5,352,189.

FIELD OF THE INVENTION

This invention relates generally to the field of orthopedic restraint apparatus, and in particular to an ankle brace for securing a patient's ankle and foot against relative movement during recovery and rehabilitation.

BACKGROUND OF THE INVENTION

Ankle injuries typically involve fractures of the tibia and fibula, malleolar fractures, and strain, tearing or rupture of one or more connective ligaments. After reduction of the fracture and repair of ligaments, the injury is treated by holding the foot in a neutral position and immobilizing the ankle in a rigid cast from below the knee to the toes. The rigid cast, which is typically molded plaster or resin, is replaced from time to time over a period of several weeks as swelling is reduced. Such rigid casts are heavy, limit the mobility of the patient, and may cause joint stiffening and muscle atrophy.

After the injured joint has stabilized, it has been found that recovery and rehabilitation can be improved by gradually permitting the injured joint to bear progressively more weight during walking movement. Traditionally, this has been carried out by replacing the bent knee long-leg cast with a tibial walking cast. Typically, two or more walking casts may be required over the course of full recovery to accommodate shrinking of the limb caused by muscle atrophy. That is, due to the rigid nature of the molded plaster or resin casts, any loosening which may result from reduction of swelling or muscle atrophy will require cast replacement to maintain the snug fit required to insure that the fracture heals in the neutral position.

Moreover, it will be appreciated that because of the rigid nature of the molded cast, wound treatment procedures, bathing and skin treatment must be postponed until the cast is removed.

DESCRIPTION OF THE PRIOR ART

For the foregoing reasons, removable fracture braces have been provided for immobilizing the ankle joint during recovery and rehabilitation. Typically, removable ankle braces include a foot plate for supporting the foot, a rigid outsole portion attached to the foot plate for permitting rolling contact with the ground during walking, and side braces attached to the foot plate including fasteners wrapped around the lower leg to firmly attach the walker to the patient's leg while securing the ankle and foot against relative movement. The ankle joint is held at a fixed angle of about 90 degrees and is stabilized to limit motion in any direction. Walking movement is accommodated by the rounded bottom configuration of the rigid outsole.

Such conventional removable ankle braces have been used primarily for stabilization of ankle and foot fractures following surgery. They also are in widespread use during rehabilitation of severe ankle sprains and ligament damage. Because such ankle braces are removable and adjustable, the ankle brace can be quickly removed to accommodate treatment of wounds, bathing, skin treatment and examination. Moreover, the ankle braces can be removed to permit a variety of wound treatments, including relief of edema, intervention and treatment of infection, massage therapy, application of cold therapy ice packs, hot packs, hydromassage and the like. Moreover, the degree of restraint or closeness of fit can be adjusted from time to time to accommodate changes caused by tissue swelling or muscle atrophy.

In the selection of materials for constructing removable fracture braces, consideration has been given to providing sufficient strength to support the patient's body weight under normal and adverse conditions. Because of the need to completely immobilize the ankle joint, consideration has also been given to the prevention of excessive toe deflection. A further consideration is reduction of the additional weight burden imposed by the walker, and the transfer of impact forces and stresses from the foot plate into the lower leg, while effectively bypassing the injured ankle joint. Other considerations are patient comfort and the ability to accommodate the normal walking gait pattern of the patient.

A common failure mode in removable fracture braces is buckling failure and/or cracking at the union of side plates and upright support braces in response to impact forces and concentration of stresses at that location. Although a metal material such as steel or aluminum can provide the necessary stiffness and strength, it imposes an unacceptable weight burden. Moreover, the use of metal components interferes with X-ray procedures.

Other design criteria include stiffness and strength. The stiffness criteria governs the deflection and stability of the frame. The strength criteria governs the structural integrity, and the ability to withstand applied loads which act near the tip of the walker frame as a result of the patient walking up or down a hill.

For those reasons, moldable plastic materials continue to be preferred for the construction of removable ankle braces and walker assemblies. However, the plastic components in such conventional designs must be oversized and excessively heavy to meet minimum stiffness and strength criteria. For example, typical stiffness and strength criteria specify an allowable deflection of 0.25 inches with loading applied through the toe of the walker frame during walking up or down a hill, and with the frame being able to withstand a compression load without buckling at a design limit load of 1.25 times the maximum expected body weight of the patient. Plastic materials utilized in conventional ankle braces and walker assemblies which meet the foregoing design criteria have required thicknesses and sizes which render the assembly to be too bulky, unwieldy or too heavy for patient comfort. When the thicknesses and sizes of the plastic components were reduced in favor of patient comfort, buckling failures have occurred, along with cracking caused by stress concentrations.

A further limitation on the use of conventional ankle brace assemblies and walkers is caused by the use of rigid outsoles in an attempt to permit the patient to attempt to simulate a normal walking gait. Such rigid outsoles typically include a foot support with a curved bottom for rolling contact with the ground, to permit rocking motion of the foot. However, it has been found that the use of such rigid outsole arrangements causes anterior or posterior shifting.

A factor which previously has not been taken into account in the construction of walkers which utilize a rigid outsole in an attempt to accommodate the normal gait pattern of an average person is that heel strike, mid-stance and toe walk associated with a normal gait pattern includes lateral and medial rolling aspects as well as the rocking feature. That is, each individual may have a different gait pattern. Some individuals have heel strike on the outside of the foot and toe walk on the inside. Others strike on the inside of the foot and toe walk on the outside. Yet others walk straight down the middle of their feet. A fixed, rigid outsole cannot accommodate such individual gait patterns. Moreover, it is important that both feet be at the same elevation. Walker assemblies having a fixed, rigid outsole will cause the patient to stand with one foot slightly higher than the other, and with his hip in a cantilevered orientation. Over an extended period of time, this will cause muscle fatigue and low back pain.

A normal gait pattern is also important for the reason that it reduces the patient's energy expense. That is, the patient should not be required to learn how to walk differently to accommodate a specific device. If the patient can reduce his energy expense, he will be more comfortable while carrying out normal activities and will not cause fatigue to the injured limb. It is desirable to maintain the injured limb in a completely restful condition, while maintaining good circulation. To avoid stressing the ankle injury, it is necessary to isolate the ankle with respect to shock absorption. A reduction in shock absorption and a reduction in muscle fatigue will be obtained if the patient's normal gait pattern is accommodated.

OBJECTS OF THE INVENTION

A general object of the present invention is to provide an improved ankle brace walker assembly of lightweight, moldable plastic construction which is effective for securing the ankle and foot against relative movement during recovery and rehabilitation.

Another object of the present invention is to provide a removable ankle brace walker assembly of the character described in which lightweight, moldable plastic materials are used in the construction of the ankle brace components which will resist buckling, crippling, cracking and the like.

A related object of the present invention is to provide a foot plate assembly for use in a removable ankle brace assembly which provides for distribution of applied loads while avoiding the concentration of stresses which might result in structural failure.

Another object of the present invention is to provide a removable ankle brace walker assembly of the character described, which is constructed of lightweight, moldable plastic materials and meets or exceeds minimum strength and stiffness criteria established for the expected body weight of the patient.

Yet another object of the present invention is to provide a removable ankle brace walker assembly of the character described, which will provide effective support while accommodating the particular walking gait pattern of the patient.

Another object of the present invention is to provide an improved ankle brace walker assembly having a composite, flexible outsole which can accommodate individual gait patterns.

Still another object of the present invention is to provide an improved ankle brace walker assembly which increases the patient's comfort and reduces the patient's fatigue during recovery and rehabilitation.

SUMMARY OF THE INVENTION

The foregoing objects are achieved according to the present invention by an ankle brace assembly having a foot plate, lateral and medial side plates attached to the foot plate, and lateral and medial brace members attached to the side plates. In the exemplary embodiment, the lateral and medial side plates each have an anterior plate portion, a posterior plate portion and an intermediate plate portion. Load forces are distributed and reacted along the lateral and medial side plates, thereby avoiding the concentration of stresses which could cause cracking, buckling, crippling or the like. This is provided, according to one aspect of the invention, by forming the external edge of the intermediate plate portion in the form of a concave arch.

Preferably, the concave edge curvature is substantially in the form of an elliptical segment. According to this arrangement, the curved, nonlinear arch portion of the side plate extends from the union of the posterior plate portion with the upright brace member to the anterior plate portion. Because of the elliptical profile of the intermediate side plate portion, the shear forces imposed by an applied toe load will be distributed through the intermediate side plate portion, thereby reducing the maximum level of forces imposed at the union of the lateral and medial brace members with the lateral and medial side plates, respectively. That is, stress concentrations are avoided, and the load forces are distributed more uniformly throughout the side plate because of the convex curvature of the intermediate side plate portion.

According to yet another aspect of the present invention, the gait pattern of the patient is accommodated by a composite outsole which permits yieldable, bending contact rather than rigid, rolling contact with the ground surface. This is accomplished by a composite outsole which includes an elongated, flexible shell, a flexible heel core and a flexible foot core, with the flexible heel core and the flexible foot core being enclosed within the flexible shell in tandem relation to each other. Preferably, the heel core is made of a resilient, yieldable material and the foot Core is made of a resilient, yieldable material, with the heel core material being relatively hard as compared to the foot core material.

According to the foregoing embodiment, a fulcrum is established at the interface between the heel core and the foot core. The heel core thus absorbs the initial forces of heel impact. As the outsole is brought into full engagement against the ground surface, the interface between the heel core and the foot core defines a fulcrum line, which permits a slight downward rotation of the forward portion of the foot relative to the heel. That is, when a patient initiates heel strike, a first plane of engagement is established, and then at mid-stance, another plane of engagement is established, followed by yet another plane of engagement established at toe walk. That is, the profile of the composite, resilient outsole continues to change during the walking movement. Moreover, the composite, flexible outsole is bendable laterally an medially with respect to the longitudinal centerline, thereby accommodating lateral or medial toe walk gait aspects. This arrangement provides a dynamic fulcrum effect which accommodates the personal gait pattern of the patient.

According to yet another aspect of the invention, the patient's comfort is increased and the patient's fatigue is reduced during recovery and rehabilitation by a protective wrap which is interposed between the patient's lower leg, ankle and foot and the surrounding ankle brace assembly. The protective wrap utilizes a sheet of resilient padding material having a leg enclosure section, an ankle enclosure section, a foot enclosure section and a heel flap. The heel flap has an apex portion secured to the leg wrap portion along a bifurcated seam, thereby avoiding contact against a stitched seam. Ventilation and aspiration of the limb is provided by the resilient padding material which is a composite lamination including an open cell polyester foam core sandwiched between an outer layer of brushed nylon fabric and an inner layer of polyester fabric.

Operational features and advantages of the present invention will be appreciated by those skilled in the art upon reading the detailed description which follows with reference to the attached drawings.

BRIEF DESCRIPTION OF THE DRAWINGS

FIG. 1 is a perspective view of a removable ankle brace walker assembly constructed according to the teachings of the present invention;

FIG. 2 is a left side elevational view thereof;

FIG. 3 is a front elevational view thereof;

DETAILED DESCRIPTION OF THE EMBODIMENTS

Figure 4:
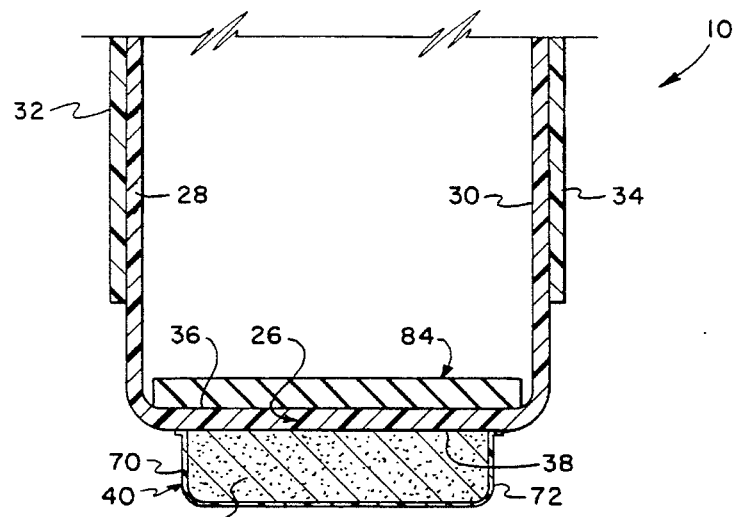
FIG. 4 is a sectional view thereof, taken along the line 4—4 of FIG. 2.

In the description which follows, like parts are marked throughout the specification and drawings with the same reference numerals, respectively. The drawings are not necessarily to scale and the proportions of certain parts have been exaggerated to better illustrate details and features of the invention.

Apparatus constructed to the preferred embodiment of the present invention in the form of an ankle brace assembly 10 is shown generally in FIG. 1, FIG. 2 and FIG. 3. For convenience in describing and illustrating the preferred embodiment, the ankle brace assembly 10 will be illustrated and described without reference to certain other components which are necessary for proper use. For example, referring to FIG. 13, the complete assembly includes a leg wrap 12, closure straps 14, 16 and 18, ankle straps 20, 22 and a foot strap 24. It will be understood that the leg wrap is first fitted about the patient's leg and foot, which is then inserted into the ankle brace assembly 10, with the foot, ankle and leg being held in a neutral, right angle orientation. The closure straps 14, 16 and 18, the ankle straps 20, 22 and the foot strap 24 are then tightened to provide a close fit, so that the ankle and foot are secured against relative displacement, without impeding circulation or otherwise causing patient discomfort.

It will be understood that the closure straps 14, 16 and 18 and ankle straps 20, 22 are secured to the upright side brace members 32, 34 by suitable fasteners, for example, plastic rivets. Moreover, the straps are preferably fitted with VELCRO hook and loop fastener elements for interlocking engagement.

Referring again to FIG. 1, FIG. 2 and FIG. 3, the ankle brace assembly 10 includes a foot plate 26, lateral and medial side plates 28, 30 and lateral and medial brace members 32, 34. The foot plate has a flat, planar top surface 36 for supporting a patient's foot, and a flat, bottom planar surface 38 for attachment to a composite outsole 40.

The lateral and medial side plates project upright with respect to the foot plate 26, preferably at a right angle. The lateral and medial brace members are rigidly attached to the lateral and medial side plates 28, 30, preferably in an adhesive, lap union. An example of a suitable epoxy adhesive is Fusor 320/321 modified epoxy structural adhesive manufactured by Lord Industrial Adhesives. This adhesive is a primer-less, two part modified epoxy based structural adhesive designed to bond metal and plastic materials. The epoxy lap bond is preferred over a mechanical fastener, and provides a stronger union since penetration to receive a mechanical fastener is not required.

Figure 7:
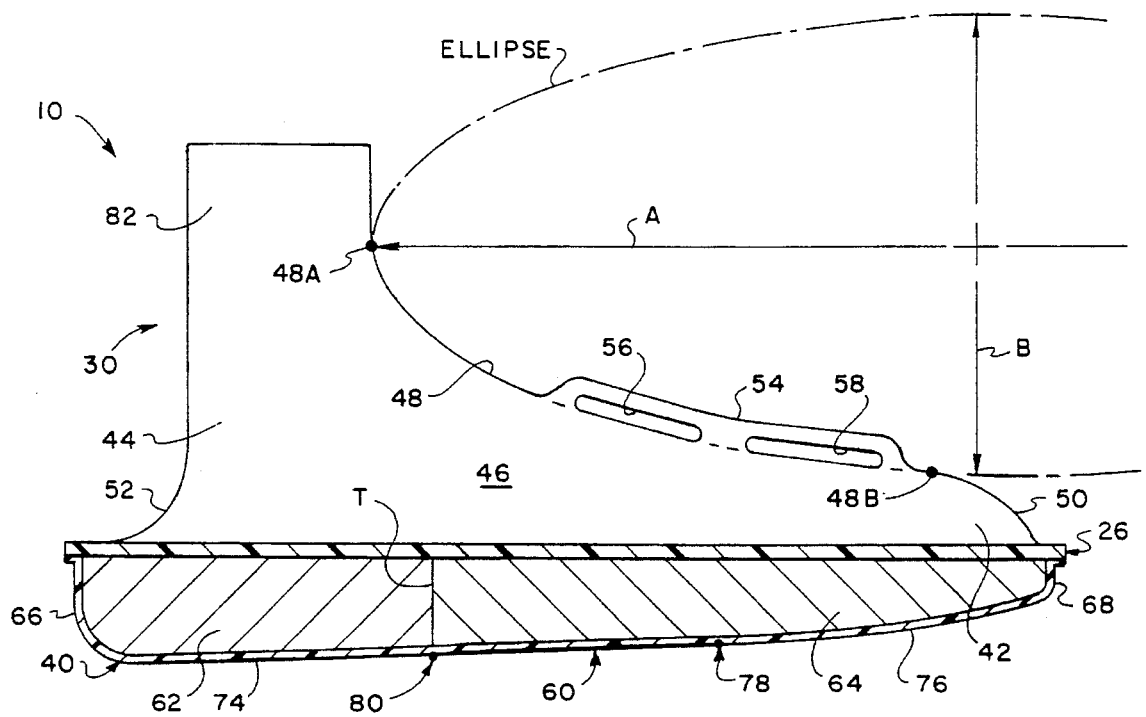
FIG. 7 is an elevational view, partly in section and taken along the line 7—7 of FIG. 8, of the foot plate assembly of FIG. 1.
Figure 8:
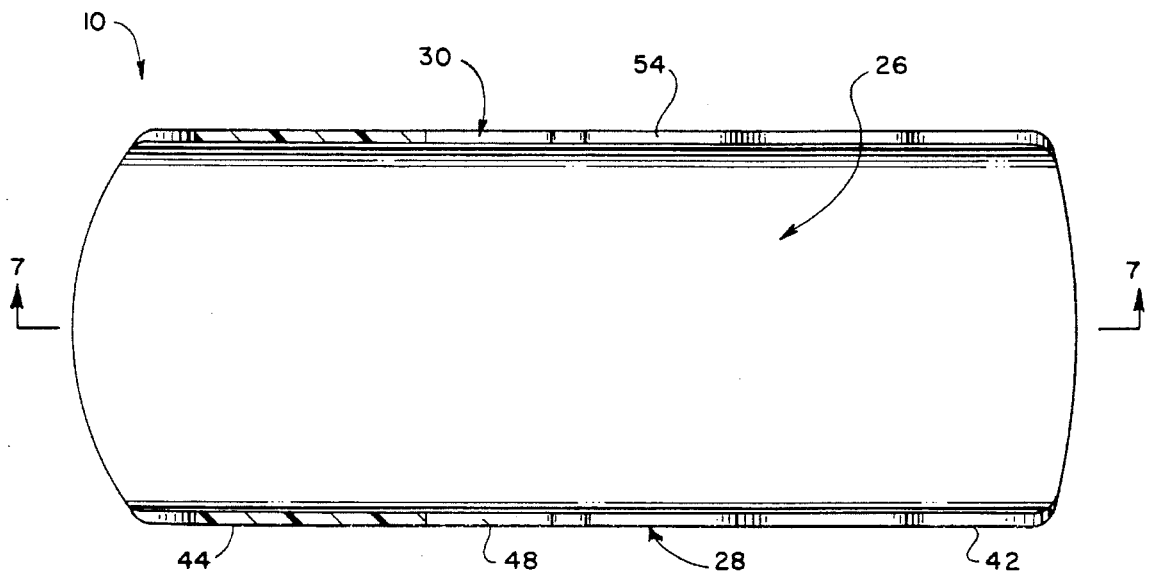
FIG. 8 is a sectional view thereof, taken along the line 8—8 of FIG. 2.
Figure 9:
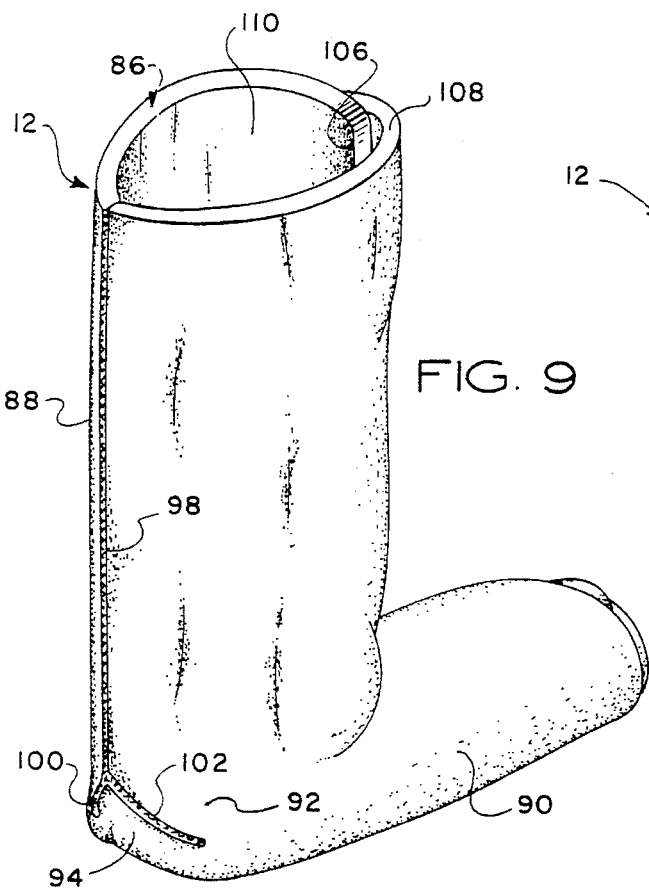
FIG. 9 is a rear perspective view of a protective wrap for fitting about the foot, ankle and lower leg of a patient prior to attachment of the ankle brace assembly.
Figure 10:
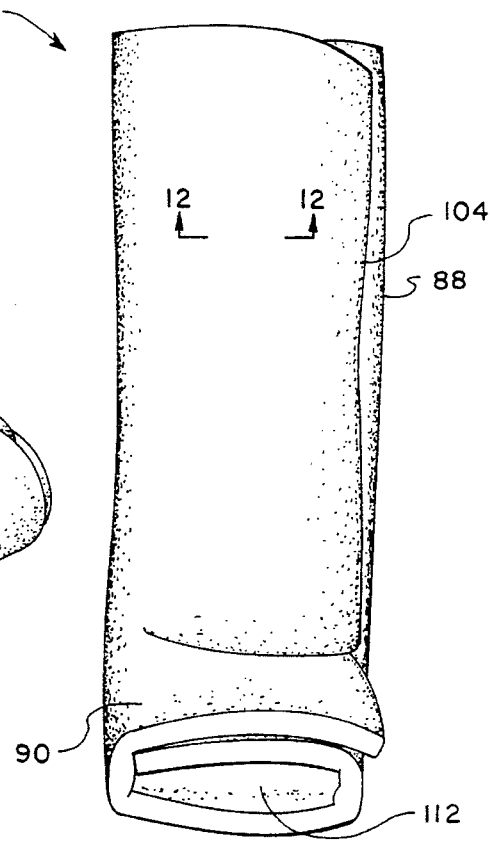
FIG. 10 is a front elevational view thereof.
Figure 11:
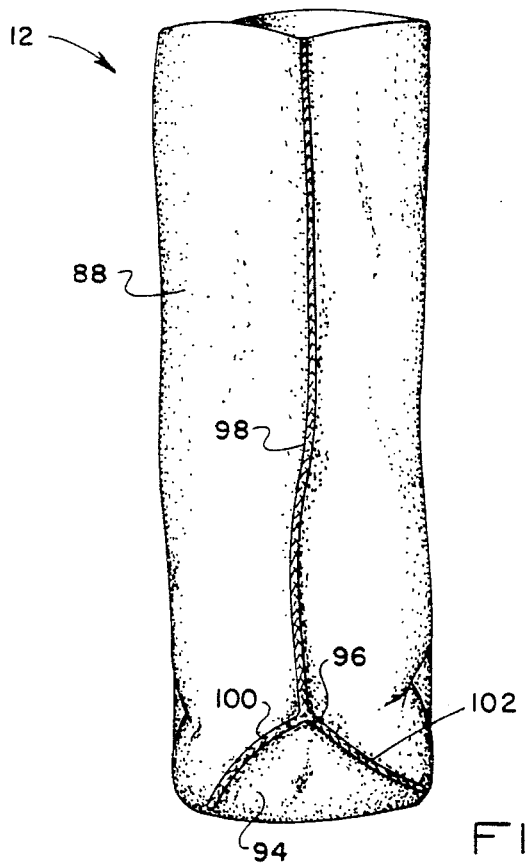
FIG. 11 is a rear elevational view thereof.
Figure 12:
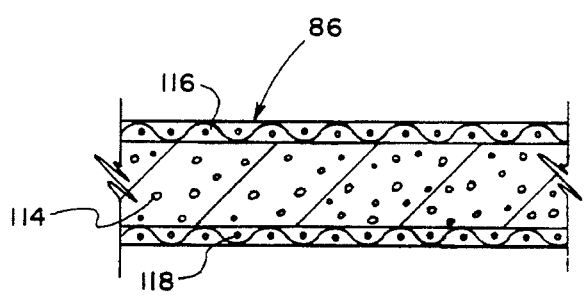
FIG. 12 is a sectional view of a composite lamination sheet of resilient padding material taken along the line 12—12 of FIG. 10; and, FIG. 13 is a perspective view of the ankle brace walker assembly of the present invention, including the installation of a protective leg wrap, closure straps, ankle straps and a forefoot strap.

The foot plate, side plates and brace members can be constructed of any high strength material, for example, various extrudable polymer materials having a thickness of about 0.15 inch. Typical dimensions for small, medium and large design ankle brace walker assemblies are as follows:

(<200 lb.) Small—4" inside width×9½" length (200+lb.) Medium—4½" inside width×10⅓" length (250 lb.) Large—4½" inside width×11⅓" length Referring now to FIG. 7 and FIG. 8, the lateral and medial side plates each have an anterior plate portion 42, a posterior plate portion 44 and an intermediate plate portion 46. The intermediate plate portion is integrally formed with the posterior plate portion and the anterior plate portion. According to an important feature of the invention, the intermediate plate portion 46 has an external edge 48 which transitions along a concave arch extending from the posterior plate portion 44 to the anterior plate portion 42. As can be seen in FIG. 7, the edge 48 follows the form of an oval segment, and preferably has a curvature substantially in the form of an elliptical segment. Because of the thickness of the side plate 28, the external edge 48 has a surface curvature substantially in the form of a concave, ellipsoidal surface. The elliptical line segment 48 extends between the points 48A and 48B, which lie between the major axis A intersection and the minor axis B intersections with the ellipse.

The anterior plate portion 42 of each side plate has an external edge 50 which transitions along a convex arch leading from the plate portion to the foot plate 26. Preferably, the convex arch 50 of the anterior plate portion has a substantially constant radius of curvature, transitioning smoothly from the terminal end 48B of the elliptical edge 48.

The posterior plate portion 44 has an external edge 52 which transitions along a concave arch leading from the posterior plate portion to the foot plate 26. Preferably, the concave arch of the posterior plate portion 52 has a substantially constant radius of curvature.

Figure 13:
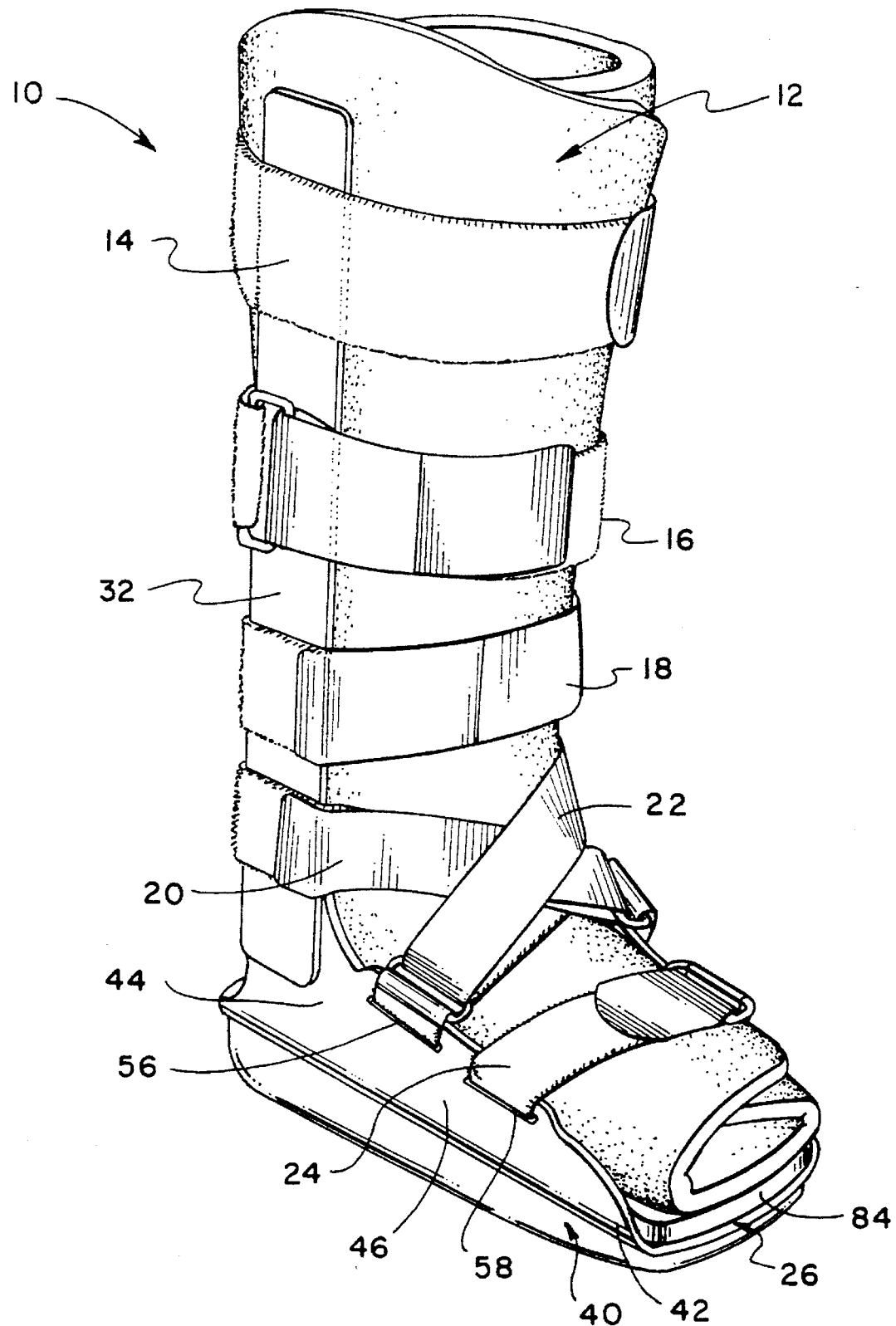

Referring again to FIG. 7, an elongated flange 54 is connected to the intermediate plate portion 46 on each side plate. The elongated flange 54 projects upright in right angle relation to the foot plate 26, and is intersected by first and second slots 56, 58 which are adapted for receiving the ankle straps 20, 22 and foot strap 24 as shown in FIG. 13.

Figure 5:
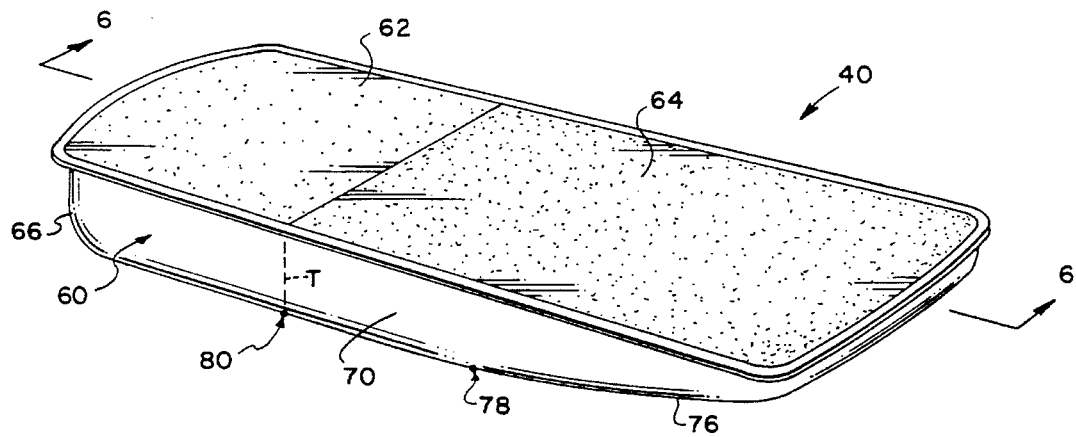
FIG. 5 is a perspective view of a composite outsole which has been removed from the walker assembly of FIG. 1.
Figure 6:
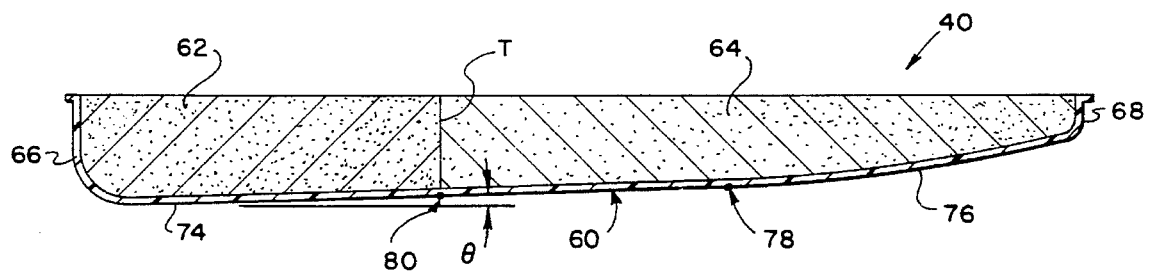
FIG. 6 is a sectional view thereof, taken along the line 6—6 of FIG. 5.

Referring now to FIG. 4, FIG. 5 and FIG. 6, the composite outsole 40 is attached to the underside surface 38 of the foot plate 26. The composite outsole includes an elongated, flexible shell 60 of a hard, durable material, for example, ethylene-vinyl acetate copolymer (EVA). The EVA shell 60 provides a non-skid ground interaction surface between a flexible heel core 62 and a flexible foot core 64. As can best be seen in FIG. 6, the flexible heel core 62 and the flexible foot core 64 are enclosed within the flexible shell 60 in tandem relation to each other.

Preferably, the heel core 62 is a molded body of cellular foam, and the foot core 64 is a molded body of cellular foam. The density of the cellular foam in the heel core 62 is greater than the density of the cellular foam in the foot core 64. This is preferred since the heel core absorbs the greatest shock forces and impact during walking activity. Preferably, the cellular foam in the heel core and in the foot core is polyethylene, and the density of the heel core cellular foam is about 8 pounds per cubic foot, and the density of the foot core cellular foam is about 3 pounds per cubic foot.

In the embodiment shown in FIGS. 4, 5 and 6, the flexible shell 60 has a heel sidewall portion 66, a toe sidewall portion 68, lateral and medial sidewalls 70, 72, a first bottom panel portion 74 and a second bottom panel portion 76. The first bottom panel portion 74 is substantially planar, and the second bottom panel portion 76 has a convex curvature. The planar bottom panel portion 74 is joined to the convex bottom panel portion 76 along a fulcrum line 78 which extends transversely across the bottom of the foot core 64. The fulcrum line lies intermediate the toe sidewall portion 68 and the tandem interface T between the heel core 62 and the foot core 64.

Preferably, the planar bottom panel portion 74 slopes inwardly toward the toe sidewall portion 68 by an acute angle θ with respect to the bottom planar surface 38 of the foot plate. The angle of inclination is preferably about 2 degrees.

The slight 2 degree inclination is desirable to compensate or offset the difficult loading which occurs as the patient walks up a hill, wherein all of the patient's weight is shifted near the toe during a toe off movement.

The interface T between the heel core 62 and the foot core 64 produces a fulcrum line 80 which extends laterally across the bottom planar portion 74. As the outsole 40 is brought into full engagement against the ground surface, the interface between the relatively hard heel core and the relatively soft foot core permits a slight downward rotation of the foot plate and forward portion of the outsole relative to the heel portion. As the patient initiates the heel strike, a first plane of engagement is established, and then at mid-stance, another plane of engagement is established as the relatively soft foot core portion is compressed, followed by yet another plane of engagement established at toe walk and push off. That is, the profile of the composite, resilient outsole 40 continues to change during walking movement, thereby producing a dynamic fulcrum effect. Because the shell 60 is flexible, and the foot core and heel core are flexible, the outsole 40 is bendable longitudinally, laterally and medially, thereby accommodating lateral and medial toe walk gait aspects.

Referring again to FIG. 7, the posterior plate portion of each sie plate has a coupling plate portion 82 which projects upright relative to the intermediate plate portion 46. The lower end of the lateral side brace member 32 forms a lapped, adhesive bond with the coupling plate portion 82.

Referring to FIG. 4 and FIG. 13, the patient's comfort is improved by an inner sole 84 adhesively attached to the upper planar surface 36 of the foot plate 26. The inner sole preferably is a body of cellular foam material having a hardness durometer of about 12 on the Shore "0" scale. The purpose of the inner sole is for comfort and shock absorption. The hardness and thickness of the inner sole is selected so that it will not bottom out upon walking impact. The inner sole 84 permits cushioning and sinking action of the foot relative to the foot plate, thereby preventing sliding movement or slipping of the foot relative to the foot plate. Preferably, the inner sole 84 is a single layer of cellular urethane.

It will be appreciated that if the outsole 40 were fixed and rigid, one foot would stand higher than the other and the patient's hip would become cantilevered. This problem is overcome in the present invention by providing that the outsole 40 is flexible and resilient, and the inner sole 84 is also flexible and resilient. When the patient stands on the ankle brace assembly, the patient's foot sinks slightly into the inner sole 84, and the outsole 40 compresses slightly because of the patient's body weight. The vertical space that the foot is supported from the ground thus automatically adjusts to be substantially equal with the other foot. That is, both feet will be at substantially the same elevation, thereby providing equal loading on both feet. This avoids muscle fatigue and low back pain.

Referring now to FIGS. 9, 10, 11 and 12, the patient's comfort is increased and the patient's fatigue is reduced during recovery and rehabilitation by the protective wrap 12 which is interposed between the patient's lower leg, ankle and foot, and the surrounding ankle brace assembly. The protective wrap 12 is formed from a single unitary sheet of resilient padding material 86 having a leg enclosure section 88, a foot enclosure section 90 and an ankle enclosure section 92. The foot enclosure section 90 is joined to the leg enclosure section 88 and the ankle enclosure section 92 by a heel flap 94. The heel flap 94 has an apex portion 96 secured to the leg wrap portion 88 and the foot wrap portion 90 along a bifurcated seam 98 having bifurcated stitch segments 100, 102.

The leg wrap 12 has a continuous front opening 104 extending its full length, formed by the overlapping sidewalls 106, 108, so that the front portion of the wrap can open part continuously from the upper leg Opening 110 at the top of the wrap, and likewise along the foot enclosure section 90 to the lower opening 112 near the end of the foot section 90.

Preferably, the resilient padding material 86 is a composite lamination comprising an open cell polyester foam core 114 sandwiched between an outer layer 116 of brushed nylon fabric and an inner layer 118 of polyester fabric. Ventilation and aspiration of the limb is provided by the wicking action of the open cell foam and the porous nylon fabric and polyester fabric.

From the foregoing discussion, it will be seen that the ankle brace walker assembly 10 of the present invention provides a lightweight, moldable plastic construction which is effective for securing a patient's ankle and foot against relative movement during recovery and rehabilitation. The lightweight, moldable plastic materials are arranged to provide for stress relief and distribution of load forces, thereby resisting buckling, crippling, cracking and the like. The elliptical profile of the lateral and medial side plates distribute applied loads more uniformly, while avoiding the concentration of stresses which might result in structural failure. The walker assembly is constructed entirely of lightweight, moldable plastic materials which meet or exceed the minimum strength and stiffness criteria established for the expected body weight of the patient. Moreover, the composite, flexible outsole provides effective support while accommodating individual gait patterns thus reducing the patient's energy expenditure, increasing the patient's comfort and reducing the patient's fatigue during recovery and rehabilitation.

What is claimed is:

1. An ankle brace assembly for securing a patient's ankle and foot against relative movement comprising, in combination:

a foot plate having a planar surface for supporting the patient's foot;

lateral and medial side plates attached to said foot plate on opposite sides of said planar surface, said lateral and medial side plates projecting upright with respect to said foot plate;

said lateral and medial side plates each formed as one piece and having an anterior plate portion, a posterior plate portion, and an intermediate plate portion integrally formed with the anterior plate portion and the posterior plate portion, the posterior plate portion having a coupling plate portion projecting upright relative to the intermediate plate portion, each side plate having an external edge which transitions along a continuous concave arch extending along the intermediate plate portion from the anterior plate portion to the coupling plate portion; and lateral and medial brace members attached to the posterior plate portions of said lateral and medial side plates, respectively, said lateral and medial brace members projecting upright with respect to said foot plate.

2. An ankle brace assembly as defined in claim 1, wherein the concave arch has a curvature substantially in the form of an oval segment.

3. An ankle brace assembly as defined in claim 1, wherein the concave arch has a curvature substantially in the form of an elliptical segment.

4. An ankle brace assembly as defined in claim 1, wherein the external edge of each intermediate plate portion transitions along the concave arch having a surface curvature substantially in the form of a concave ellipsoidal surface.

5. An ankle brace assembly as defined in claim 1, wherein the external edge of each side plate transitions along the continuous concave arch having a curvature substantially in the form of an elliptical segment lying between a major axis and a minor axis of an ellipse, the external edge transitioning from the concave arch to the edge of the coupling plate at a point of intersection between the external edge and the major axis.

6. An ankle brace assembly as defined in claim 1, the anterior plate portion of each side plate having an external edge which transitions along a convex arch from the external edge of the intermediate plate portion to said foot plate.

7. A foot plate assembly as defined in claim 6, wherein the convex arch of the anterior plate portion has a substantially constant radius of curvature.

8. An ankle brace assembly as defined in claim 1, wherein the posterior plate portion has an external edge which transitions along a concave arch leading from the posterior plate portion to said foot plate.

9. A foot plate assembly as defined in claim 8, wherein the concave arch of the posterior plate portion has a substantially constant radius of curvature.

10. An ankle brace assembly as defined in claim 1, wherein the lateral and medial side plates are integrally formed with said foot plate.

11. An ankle brace assembly as defined in claim 1, wherein the lateral and medial side plates project upright substantially in right angle relationship with the planar surface of said foot plate, respectively.

12. An ankle brace assembly as defined in claim 1, including an elongated flange connected to the intermediate plate portion of each side plate, respectively, each elongated flange projecting upright with respect to said foot plate and each elongated flange being intersected by first and second slots, said slots being adapted for receiving fastener straps.

13. An ankle brace walker assembly comprising, in combination:

a foot plate having a first planar surface for supporting a patient's foot and having a second planar surface for attachment to an outsole;

lateral and medial side plates attached to said foot plate on opposite sides of said first planar surface, said lateral and medial side plates projecting upright with respect to said foot plate;

lateral and medial brace members attached to said lateral and medial side plates, respectively, said lateral and medial brace members projecting upright with respect to said foot plate; an a composite outsole attached to the second side surface of said foot plate, said composite outsole including an elongated, flexible shell, a flexible heel core and a flexible foot core, the flexible heel core and flexible foot core being enclosed within the flexible shell in tandem relation to each other;

wherein said heel core comprises a first resilient, yieldable material and said foot core comprises a second resilient, yieldable material, with the first material being significantly more resilient and significantly less yieldable than the second material.

14. An ankle brace walker assembly as defined in claim 13, wherein said heel core comprises a first body of cellular foam having a first density, and said foot core comprises a second body of cellular foam having second density, wherein the first density is greater than the second density.

15. An ankle brace walker assembly as defined in claim 14, wherein the first density and the second density are in the range of about 3 pounds per cubic foot to about 8 pounds per cubic foot.

16. An ankle brace walker assembly as defined in claim 14, wherein the first density is about 8 pounds per cubic foot, and the second density is about 3 pounds per cubic foot.

17. An ankle brace walker assembly as defined in claim 14, wherein said first and second bodies of cellular foam comprise polyethylene.

18. An ankle brace walker assembly as defined in claim 13, including an inner sole disposed on the first planar surface of said foot plate, said inner sole comprising a body of cellular foam material having a hardness durometer of about 12 on the Shore "0" scale.

19. An ankle brace walker assembly as defined in claim 18, wherein said body of cellular foam material comprises microcellular urethane.

20. An ankle brace assembly for securing a patient's ankle and foot against relative movement comprising, in combination:

a foot plate having a planar surface for supporting the patient's foot;

lateral and medial side plates attached to said foot plate on opposite sides of said planar surface, said lateral and medial side plates projecting upright with respect to said foot plate;

lateral and medial brace members attached to said lateral and medial side plates, respectively, said lateral and medial brace members projecting upright with respect to said foot plate; and, said lateral and medial side plates each formed as one piece and having an anterior plate portion, a posterior plate portion, and an intermediate plate portion integrally formed with the anterior plate portion and the posterior plate portion, the posterior plate portion having a coupling plate portion projecting upright relative to the intermediate plate portion, and the intermediate plate portion of each side plate having an external edge which transitions along a continuous concave arch leading from the coupling plate portion to the anterior plate portion, the external edge becoming substantially straight at the coupling plate portion.

21. An ankle brace walker assembly comprising, in combination:

a foot plate having a first planar surface for supporting a patient's foot and having a second planar surface for attachment to an outsole;

lateral and medial side plates attached to said foot plate on opposite sides of said first planar surface, said lateral and medial side plates projecting upright with respect to said foot plate;

lateral and medial brace members attached to said lateral and medial side plates, respectively, said lateral and medial brace members projecting upright with respect to said foot plate; and, a composite outsole attached to the second planar surface of said foot plate, said composite outsole including an elongated, flexible shell, a flexible heel core and a flexible foot core, the flexible heel core and the flexible foot core being enclosed within the flexible shell in tandem relation to each other, wherein said heel core comprises a first resilient, yieldable material and said foot core comprises a second resilient, yieldable material, with the first material being significantly more resilient and significantly less yieldable than the second material.

22. An ankle brace walker assembly comprising, in combination:

a foot plate having a first planar surface for supporting a patient's foot and having a second planar surface for attachment to an outsole;

an outsole attached to the second planar surface of said foot plate;

lateral and medial side plates attached to said foot plate on opposite sides of said first planar surface, said lateral and medial side plates projecting upright with respect to said foot plate;

lateral and medial brace members attached to said lateral and medial side plates, respectively, said lateral and medial brace members projecting upright with respect to said foot plate; and, said lateral and medial side plates each formed as a single piece and having an anterior plate portion, a posterior plate portion, and an intermediate plate portion integrally formed with the posterior plate portion and the anterior plate portion, each posterior plate portion having a coupling plate portion projecting upright relative to the intermediate plate portion, each side plate having an external edge which transitions along a continuous concave arch leading from the coupling plate portion to the anterior plate portion, the external edge becoming substantially straight and perpendicular to the foot plate along the coupling plate portion beyond the concave arch.

23. A protective wrap for fitting about the foot, ankle and lower leg of a patient comprising a single unitary sheet of resilient padding material having a leg enclosure section for wrapping around the lower leg and extending from below the knee joint to approximately the instep region of the foot above the ankle, an L-shaped ankle enclosure section for wrapping about the ankle, and a foot enclosure section, said protective wrap having a continuous front opening extending its full length so that the front portion of the wrap can open apart continuously from an upper opening at the top of the wrap, along the ankle enclosure section and the foot enclosure section of the wrap, to a lower opening near the end of the foot section, with one side of the upper enclosure section being formed as a flexible upper wrap to overlap the opposite side along the front opening to form a long, straight closure extending along the front of the leg enclosure section, one side of the foot enclosure section being formed as a flexible lower flap to form a closure extending along the top of the foot section, with the foot enclosure section being joined to the leg enclosure section by a heel flap portion, said heel flap transitioning through substantially a right angle from the foot wrap portion to the leg wrap portion, and having an apex portion secured to the leg wrap portion and the foot wrap portion along a bifurcated seam.

24. A protective wrap as defined in claim 23, wherein the resilient padding material is a composite lamination comprising an open cell polyester foam core sandwiched between an outer layer of brushed nylon fabric and an inner layer of polyester fabric.

25. An ankle brace walker assembly comprising:

a foot plate having a first surface for supporting a patient's foot and a second surface for attachment to an outsole;

a pair of side plates attached to said foot plate on opposite sides of said first surface, said side plates projecting from said first surface;

a pair of brace members attached respectively to one of said side plates and projecting from said foot plate in the same direction as said side plates; and a composite outsole attached to the second surface of said foot plate, said composite outsole having a thickness substantially greater than the thickness of the associated foot plate in order to provide enhanced cushioning to the walker assembly and having an elongated, flexible shell, a flexible heel core and a flexible foot core enclosed within the flexible shell in tandem relationship with each other, said heel core comprising a resilient, yieldable material and said foot core comprising a resilient, yieldable material, with the heel core material being relatively hard as compared to the foot core material.

26. The ankle brace walker assembly as defined in claim 25 further comprising:

an inner sole disposed on the first surface of said foot plate; and the thickness of the foot plate substantially reduced as compared to the thickness of said inner sole and said composite outsole whereby the overall thickness of said inner sole, said footplate, and said composite outsole may be minimized.

27. The ankle brace walker assembly as defined in claim 25, wherein said composite outsole extends over the second surface and provides resilient means for substantially equalizing the vertical support of said patient's feet.

28. The ankle brace walker assembly as defined in claim 25, further comprising the foot plate, side plates and brace members having approximately the same thickness with respect to each other.

29. The ankle brace walker assembly as defined in claim 25, wherein said heel core comprises a body of cellular foam, and said foot core comprises a body of cellular foam, the density of the cellular foam in said heel core being greater than the density of the cellular foam in said foot core.

30. The ankle brace walker assembly as defined in claim 29, wherein the density of the cellular foam material in the heel core and the density of the cellular foam material in the foot core are in the range of from about 3 pounds per cubic foot to about 8 pounds per cubic foot.

31. The ankle brace walker assembly as defined in claim 29, wherein said bodies of cellular foam comprise polyethylene.

32. The ankle brace walker assembly as defined in claim 25, further comprising:

an inner sole disposed on the first surface of said foot plate; and said inner sole and said composite outsole cooperating to provide additional resilient means for substantially equalizing the vertical support of said patient's feet.

33. The ankle brace walker assembly as defined in claim 32, wherein said inner sole further comprises a body of cellular foam material.

* * * * *

UNITED STATES PATENT AND TRADEMARK OFFICE
CERTIFICATE OF CORRECTION

PATENT NO. : 5,620,411
DATED : April 15, 1997
INVENTOR(S) : Schumann, et al.

It is certified that error appears in the above-identified patent and that said Letters Patent is hereby corrected as shown below:

Title page, item: [56], delete "4,771,468 " and insert
-- 4,771,768 --.

Column 6, line 58, after "the", insert -- intermediate --;

Column 6, line 58, after "portion", insert -- 46 --;

Column 6, line 59, after "portion", insert -- 42 --.

Column 8, line 48, delete "part", and insert -- apart --.

Column 10, line 26, after "plate;", delete "an" and insert
-- and --

Column 10, line 41, after "having" insert -- a --.

Signed and Sealed this

Twenty-sixth Day of August, 1997

Attest:

BRUCE LEHMAN

*Attesting Officer*  *Commissioner of Patents and Trademarks*